(12) United States Patent
Correale

(10) Patent No.: US 8,586,915 B2
(45) Date of Patent: Nov. 19, 2013

(54) GAS SAMPLING DEVICE AND GAS ANALYZER EMPLOYING THE SAME

(75) Inventor: Raffaele Correale, Turin (IT)

(73) Assignee: Agilent Technologies, Inc., Santa Clara, CA (US)

( * ) Notice: Subject to any disclaimer, the term of this patent is extended or adjusted under 35 U.S.C. 154(b) by 160 days.

(21) Appl. No.: 12/831,945

(22) Filed: Jul. 7, 2010

(65) Prior Publication Data

US 2011/0006202 A1 Jan. 13, 2011

(30) Foreign Application Priority Data

Jul. 8, 2009 (IT) ............................... TO2009A0513
May 13, 2010 (IT) ............................... TO2010A0399

(51) Int. Cl.
*B01D 59/44* (2006.01)
*B01D 59/12* (2006.01)
*H01J 49/00* (2006.01)

(52) U.S. Cl.
USPC ........... 250/288; 250/281; 250/282; 250/283; 95/45

(58) Field of Classification Search
USPC .......... 250/281–283, 288, 423 R, 424; 95/43, 95/45, 291
See application file for complete search history.

(56) References Cited

U.S. PATENT DOCUMENTS

| 3,455,092 | A | 7/1969 | Llewellyn |
| 3,712,111 | A | 1/1973 | Llewellyn |
| 3,751,880 | A | 8/1973 | Holm |
| 4,008,388 | A | * 2/1977 | McLafferty et al. ............ 702/27 |
| 4,051,372 | A | 9/1977 | Aine |
| 4,311,669 | A | 1/1982 | Spangler |
| 4,551,624 | A | * 11/1985 | Spangler et al. ............... 250/287 |
| 4,712,008 | A | 12/1987 | Vora et al. |
| 4,804,839 | A | * 2/1989 | Broadbent et al. ............ 250/288 |
| 6,006,584 | A | * 12/1999 | Itoi .............................. 73/23.37 |
| 6,039,792 | A | * 3/2000 | Calamur et al. ................... 95/45 |
| 6,822,226 | B2 | 11/2004 | Ross et al. |
| 7,037,425 | B2* | 5/2006 | Lee et al. .................. 210/321.75 |
| 7,155,076 | B2* | 12/2006 | Letant et al. ..................... 385/12 |
| 7,217,919 | B2 | 5/2007 | Boyle et al. |
| 7,361,888 | B1 | 4/2008 | Boyle et al. |
| 7,528,366 | B1 | 5/2009 | Boyle et al. |

(Continued)

FOREIGN PATENT DOCUMENTS

| EP | 1764832 A2 | 3/2007 |
| JP | 2001155677 A | 6/2008 |

(Continued)

OTHER PUBLICATIONS

Madden A M et al, Sheet Materials for Use as Membranes in Membrane Introduction Mass Spectrometry Analytical Chemistry, American Chemical Society, US, vol. 48; No. 10; May 15, 1996.

(Continued)

*Primary Examiner* — Bernard E Souw

(57) ABSTRACT

A gas sampling device has a high-vacuum tight chamber formed within its casing, which communicates with an ambient outside through an inlet hole for the gas flow to be ionized and the ambient downstream the ionization chamber with an outlet hole for the ionized gas. A high-vacuum tight membrane separates the inlet hole from the ambient outside the chamber. The membrane has at least one nanohole formed therethrough with a diameter in the order of nanometers.

20 Claims, 3 Drawing Sheets

(56) References Cited

U.S. PATENT DOCUMENTS

| | | | |
|---|---|---|---|
| 7,582,867 B2 * | 9/2009 | Wells et al. | 250/292 |
| 7,690,241 B2 * | 4/2010 | Muntz et al. | 73/31.07 |
| 7,803,274 B2 * | 9/2010 | Taylor et al. | 210/321.81 |
| 8,237,116 B2 * | 8/2012 | Correale | 250/288 |
| 8,337,588 B2 * | 12/2012 | Shqau et al. | 95/51 |
| 2001/0029841 A1 | 10/2001 | Li et al. | |
| 2002/0134933 A1 | 9/2002 | Jenkins et al. | |
| 2006/0091308 A1 | 5/2006 | Boyle et al. | |
| 2008/0168752 A1 | 7/2008 | Smith et al. | |
| 2008/0178658 A1 * | 7/2008 | Muntz et al. | 73/23.41 |
| 2009/0272684 A1 * | 11/2009 | Taylor et al. | 210/323.2 |
| 2009/0294657 A1 * | 12/2009 | Rafferty | 250/283 |
| 2010/0223979 A1 | 9/2010 | Ploehn et al. | |
| 2011/0006201 A1 * | 1/2011 | Correale | 250/288 |
| 2011/0006202 A1 | 1/2011 | Correale | |
| 2011/0247492 A1 * | 10/2011 | Shqau et al. | 95/51 |
| 2012/0208004 A1 * | 8/2012 | Wolcott et al. | 428/315.7 |
| 2013/0043380 A1 * | 2/2013 | Correale | 250/252.1 |

FOREIGN PATENT DOCUMENTS

| | | |
|---|---|---|
| WO | 0135441 A1 | 5/2001 |
| WO | 03049840 A1 | 6/2003 |
| WO | 2008074984 A1 | 6/2008 |

OTHER PUBLICATIONS

European Patent Office, Communication dated Aug. 18, 2010.
Notice of Allowance dated Jan. 24, 2012 for U.S. Appl. No. 12/831,921.
European Search Report dated Aug. 18, 2010.
European Interview Summary dated Jun. 1, 2012.
Response to EP Office Action dated Jul. 9, 2012.
Non-Final Office Action for U.S. Appl. No. 13/661,486.

* cited by examiner

GAS SAMPLING DEVICE AND GAS ANALYZER EMPLOYING THE SAME

CROSS REFERENCE TO RELATED APPLICATIONS

This patent application claims the benefit of the Italian priority patent application no. TO2009A000513 filed on Jul. 8, 2009, and also claims further priority to the subsequently filed Italian patent application no. TO2010A000399 filed on May 13, 2010. This patent application relates to U.S. patent application filed on Jul. 7, 2010, which is presently identified with Ser. No. 12/831,921 and is titled "GC-MS ANALYSIS APPARATUS".

TECHNICAL FIELD

The present invention concerns a gas sampling device and a gas analyzer employing the device.

BACKGROUND OF THE INVENTION

Mass spectrometry is used for analysing substances that can be brought to the gas phase under high-vacuum conditions, i.e. under pressures generally ranging between about $10^{-2}$ and $10^{-6}$ Pa. Though the invention is not limited to this field of use, reference in the following description will therefore be made mainly to this analysis method.

The mass spectrometry is a known analytical technique applied to both the identification and analysis of known substances. The principle on which it is based is the possibility of separating a mixture of ions depending on their mass/charge (m/z) ratio generally by applying electric or magnetic fields, either static or oscillating.

There are different ways to volatilise and ionise a sample, and there are many different kinds of ion sources, such as EI (Electronic Impact) source, FAB (Fast Atom Bombardment) source, electro-spray source, MALDI (Matrix Assisted Laser Desorption and Ionisation) source. One of the most frequently used sources is the electronic impact EI source, wherein the substance of the sample either spontaneously evaporates or is already in the gas phase. A known energy electron flow hits the molecules of the sample, which are changed into positive ions by losing one or more electrons. The ions are then accelerated by an electrostatic field and directed towards the analyser.

The diagram reporting the concentration of each ion versus the mass/charge ratio is, the so-called, mass spectrum distinctive of each compound, since it is directly correlated to the chemical structure thereof as well as to the ionisation conditions, which undergoes. The instruments employed in the mass spectrometry field, known as mass spectrometers, generally comprise three main units arranged in series: an ion source to volatilise and ionise the sample, an analyser to select the ions produced by the source according to the mass/charge ratio; and a detector to detect the ions coming from the analyser. The ion source is the part of the mass spectrometer entrusted to change the molecules of the sample into ions through the ionisation phenomenon. Moreover the produced ions must be free of moving in space for measurement of the m/z ratio.

The analyser is the part of the mass spectrometer allowing for selecting the mass/charge (m/z) ratio of the ions produced by the source. Also this measurement can be carried out in many ways, however it is always requested that the ions can freely move in the spectrometer without colliding with air molecules, which is activated by providing high-vacuum conditions therein.

According to the prior art, analysers are mainly classified as magnetic analysers, Omegatron analysers (the mass selection is carried out by using a magnetic field and a RF field), quadrupole analysers, ion-trap analysers, FI-ICR (Fourier Transform Ion Cyclotron Resonance) analysers, TOF (Time of Flight) analysers, cycloidal mass analysers (the mass selection is carried out through a suitable selection of the resulting electric and magnetic field), magnetic-sector and ion-trap analysers, optic spectroscopy cross-wire analysers (measurement of the spectra either of emission or absorption light or of photons effects on the analyzed sample). In the present work the reference is made, by way of example, to the magnetic quadrupole, and ion-trap analyzers.

The magnetic analyzer comprises a bent tube immersed into a magnetic field perpendicular thereto. The magnetic field makes the ions cover a bent trajectory. The bend radius depends on the entering ions energy and on the magnetic field B. The ion exits the analyzer only if the ion trajectory corresponds to the tube bend. If the ion bends more or less than the tube bends, it collides with the tube walls being neutralized. Therefore, for each value of the magnetic field only ions having a certain m/z ratio and a certain kinetic energy pass through the analyser, while the others are removed. From the value of the magnetic field and from the kinetic energy it is possible to go back to the m/z ratio of the ion selected by the analyser. In this way the mass spectrum, which is the graph of the intensity of the ionic current detected by the detector, is obtained depending on the m/z ratio selected by the analyser. In a mass spectrum, the presence of a peak at a certain value of m/z indicates that the source is producing ions having that m/z ratio.

Another kind of analyser frequently employed in the mass spectrometry is the quadrupole analyser. Generally, a quadrupole is a device composed of four metal parallel bars. Each couple of diagonally opposed bars is electrically linked together and a RF (radio-frequency) voltage is applied between a couple of bars and the other one. A direct current voltage is then added to RF voltage. Ions oscillate during the flight among the quadrupole bars. Only the ions having a certain m/z ratio pass through the quadrupole and reach the detector for a given ratio of the two voltages: the other ions undergo instable oscillation and collide with the bars. This allows either the selection of a particular ion, or the scansion in the field of the masses by means of the voltages variation.

A further example of mass analyser consists of an ion-trap. Based on a physical principle similar to the one of the quadrupole, the ion-trap keeps all the ions within the trap and makes them selectively free upon varying of the intensity of an oscillating electric field.

The detectors generally comprise dynodes, i.e. electronic multipliers able to amplify the very feeble current produced by the ions passed through the analyser. The signals obtained in this way are subsequently transmitted to a computer able to represent, with the aid of suitable software, the amount of each ion depending on its mass, i.e. the final mass spectrum. Moreover, the use of computers allow to quickly combine the instrument parameters with the literature search in libraries of electronic format spectra, so as to automate the compounds identification according to their spectrum and to the operative conditions with which the analysis has been carried out.

With reference to FIG. 1, a mass spectrometer device of the kind based on an electronic impact source and on a quadrupole mass analyser according to the known art is schematically shown. In FIG. 1, the device is denoted as a whole with the reference numeral (11) and it comprises an entrance section (11a), an ionisation section (11b), an analysis section (11c) and a detection section (11d).

The entrance section (11a) is generally intended for being immersed in the ambient to be sampled, which generally reaches the atmospheric pressure, from which the gas to be sampled, or analyte, enters the device. To this purpose the entrance section (11a) substantially comprises a capillary tube (13) with which a heater (15) is associated. The heater, for instance, has an electric resistance wound around the capillary tube (13). As it is known, to avoid effects due to absorption/desorption along the walls of the introduction system of gas, it is advisable to make a suitable choice of the materials as well as operating at a reasonably high temperature, for instance 100° C. that further allows for avoiding gas condensation phenomena.

In accordance with a prior art embodiment, the capillary tube (13) leads to a first transition chamber (17) defined inside a corresponding flange (19), and discharged by means of a high-vacuum pump (21). The pump (21) for instance can be a turbo-molecular pump, associated through a duct (23) at a radial side door (25) and presenting the entrance axial primary door (43) associated with the casing (41) of the device.

Downstream the first transition chamber (17) a second micro-capillary tube (27), for instance having an about 20μ diameter and being about 1-2 mm long, is provided. The micro-capillary tube (27) communicates, in turn, with a second transition chamber (29), associated with the ionisation section (11b), wherein the gas to be sampled is collected downstream the micro-capillary tube (27).

In the shown example, the ionisation section (11b) comprises an electronic impact source, wherein an ionisation chamber (31) equipped with ionisation means (33), for instance ionisation filaments, is defined. Moreover, permanent magnets can be provided for increasing the source efficiency: in this way the electrons actually describe spiral trajectories so increasing the total path inside the source. Electrostatic lenses (35) are provided downstream the ionisation chamber (31) in the transition area between the ionisation chamber (33) and the following analysis section (11c). In the ionisation chamber the molecules of the sample to be analysed, which are in the gas phase, interact with an electron beam generated by an incandescent filament and accelerated through an adjustable potential. The beam energy is normally arranged between about 10 and 100 eV.

The analysis section (11c) comprises a quadrupole device (37) downstream with the detection section (11d) comprising a detector (39), for instance a faraday cup detector and/or a SEM (Second Electron Multiplier) detector or a Channeltron detector, is provided. The analysis section (11c) and the detection section (11d) are housed in the casing (41) at a pressure of generally in the order of at least $10^{-3}$ Pa, obtained through the turbo-molecular pump (21) associated through the corresponding axial primary door (43).

Calibrated leak devices are also known in the art. Devices of this kind allow to generate controlled gas flows through the membrane as well as to quantificate leakages value, by calibrating the instruments required to detect them, during tight tests. The currently used devices are substantially of two kinds: orifice leaks, or capillary, and helium permeation leaks. The first ones, also called pinholes, are generally made by laser ablation or chemical etching. Such technologies enable apertures to be manufactured with high precision and reproducibility. An example of the first kind of devices having membranes with nanoholes (holes passing through the membrane and having a nanometric size diameter) is disclosed in US Pub. No. 2006/0144120. Devices of this kind allow for generating controlled gas flows through the membrane as well as to quantificate leakages values by calibrating the instruments required to detect them during tight tests. Another example of this kind of membrane is disclosed in WO 03/049840.

The permeation leaks however have a very unstable behaviour when the temperature changes (their value varies of about 3% per centigrade grade in case of temperatures values around room temperature), long response times. They are fragile (being made of glass, they are easily breakable even when they only fall to the ground), only suitable for helium and have a single flow value. Examples of such permeation leaks are described in DE 19521275 and WO 02/03057.

Gas sampling devices based on permeation leaks are also disclosed in U.S. Pat. No. 4,008,388, US Publication No. 2002/134933, U.S. Pat. No. 4,311,669, U.S. Pat. No. 4,712,008 and WO2008/074984. Selectively permeable membranes used in the field of mass spectrometry are also disclosed in U.S. Pat. No. 4,551,624 and Maden A M et Al: "Sheet materials for use as membranes in membrane introduction mass spectrometry" Anal. Chem., Am. Chem. Soc., US vol. 68, no. 10, 15 May 1996 (1996-05-15). Pages 1805-1811, XP000588711 ISSN: 0003-2700.

Nanoholes membranes of the above first species have not to be confused with gas permeable membranes. Membranes of the first kind have holes made artificially, e.g. by laser drilling, having substantially regular cross section along the whole length of the hole and for this reason can be calibrated according to the use of the membrane. In addition, several or many practically identical holes with parallel axis can be produced on the same membrane. On the contrary, gas permeable membranes are membranes whose natural property of the material allows for permeability of a gas or a gas mixture usually at a high temperature.

As it will be easily appreciated from the preceding description of a gas analyser according to the known art, the entrance section and the ionisation section are considerably complex both for the number of the components and for the fact that such components must be high-vacuum tight associated with each other, resulting in high costs. Moreover, the prior art devices must be equipped with vacuum pumps having considerable flow capacities as they have to absorb the flow entering the ionisation chamber, which is generally high.

An object of the invention is therefore to provide a simplified sampling gas device, which can be used in numerous applications and, in particular, associated with a gas analyser.

A further object of the invention is to provide a gas sampling device, which can be industrially produced with favourable costs.

These and other objects are achieved with the gas sampling device as claimed in the appended claims.

SUMMARY OF THE INVENTION

A first advantage of the invention comes from the use of a membrane having at least a nanohole for separating the two spaces kept under differential vacuum conditions, the ambient outside the sampling device and the ionization chamber of the sampling device respectively. Due to the structure of the membrane having at least a nanohole a molecular flow is already established at atmospheric pressure, without need of using complex devices, as it instead occurs in the prior art.

The molecular flow, which is established at the membrane having at least a nanohole involves, nevertheless, an alteration of the distribution of the gas concentration in the gas mixture penetrating inside the ionization chamber of the sampling device. Since, in fact, under molecular regime the gas flow inside the chamber of the sampling device is inversely proportional to the square root of the masses, it is evident that lighter gases will have a higher concentration inside the chamber (for instance, an amount of helium higher than argon). In many applications this alteration of the distribution of the gas concentration, relative to the sampling ambient, is unwanted and it is therefore required to intervene for restoring the right distribution, for instance by means of calculation algorithms.

Advantageously, however, according to a preferred embodiment of the present invention the chamber of the sampling device is provided with a calibrated exit hole towards the analyser or mass filter, for instance quadrupole under high or ultra-high-vacuum conditions, wherein a molecular flow remains and that thus determines the restoration of the appropriate conditions of distribution of the concentration inside the chamber of the sampling device. In this embodiment of the invention, there is therefore no need of rectifying the distribution of the gas concentration.

Advantageously, due to utilization of a membrane having at least a nanohole and preferably a plurality of nanoholes (nanoholes membrane), associated with the ionisation chamber, many components of known devices can be removed. In particular, the following components could be unnecessary: the capillary tube and corresponding heater, the transition flange and the relevant transition chamber and the micro-capillary tube and the corresponding connections between the transition chamber and the vacuum pump. This latter, furthermore, can be replaced with a simpler high-vacuum ionic pump, considering the low pumping rate requested to maintain high-vacuum conditions inside the device, due to the low conductance of the device according to the present invention. It will be therefore possible to remove the mechanical pump normally provided in the known systems as well as to obtain very portable devices.

Another advantage of the invention is that due to the provision that only either the membrane with at least a nanohole or the nanoholes membrane separating the two spaces kept under differential vacuum conditions, the response times of the sampling device are extremely quick (for instance, in the order of seconds or lower).

Moreover, the gas reduced flow will have clear advantages particularly in presence of corrosive gases, which are creating a deterioration problem in the known devices. The higher the gas flow passing through the device is the more damage it may cause.

The choice of either a membrane having at least a nanohole or a nanoholes membrane of the kind, wherein the diameter D and the length L of the nanohole or nanoholes have sizes such as L<20·D and the equivalent diameter $D_e$ of the orifice is $D_e \leq 100$ nm, where $D_e$ is defined by the relationship $D_e = D \cdot a^{1/2}$, wherein a is the transmission probability of the orifice, depending on the L/D ratio, the orifice is able to operate under a molecular flow regime in a whole range of $P_u$ values comprising the atmospheric pressure value, furthermore involve, a considerable reduction of the tendency of the nanoholes to occlude.

BRIEF DESCRIPTION OF THE DRAWINGS

A preferred embodiment of the invention will be now disclosed by way of non-limiting example with reference to the enclosed figures in which.

In all the figures the same reference numerals have been used to denote equal or functionally equivalent components.

DESCRIPTION OF A PREFERRED EMBODIMENT

Figure 2:
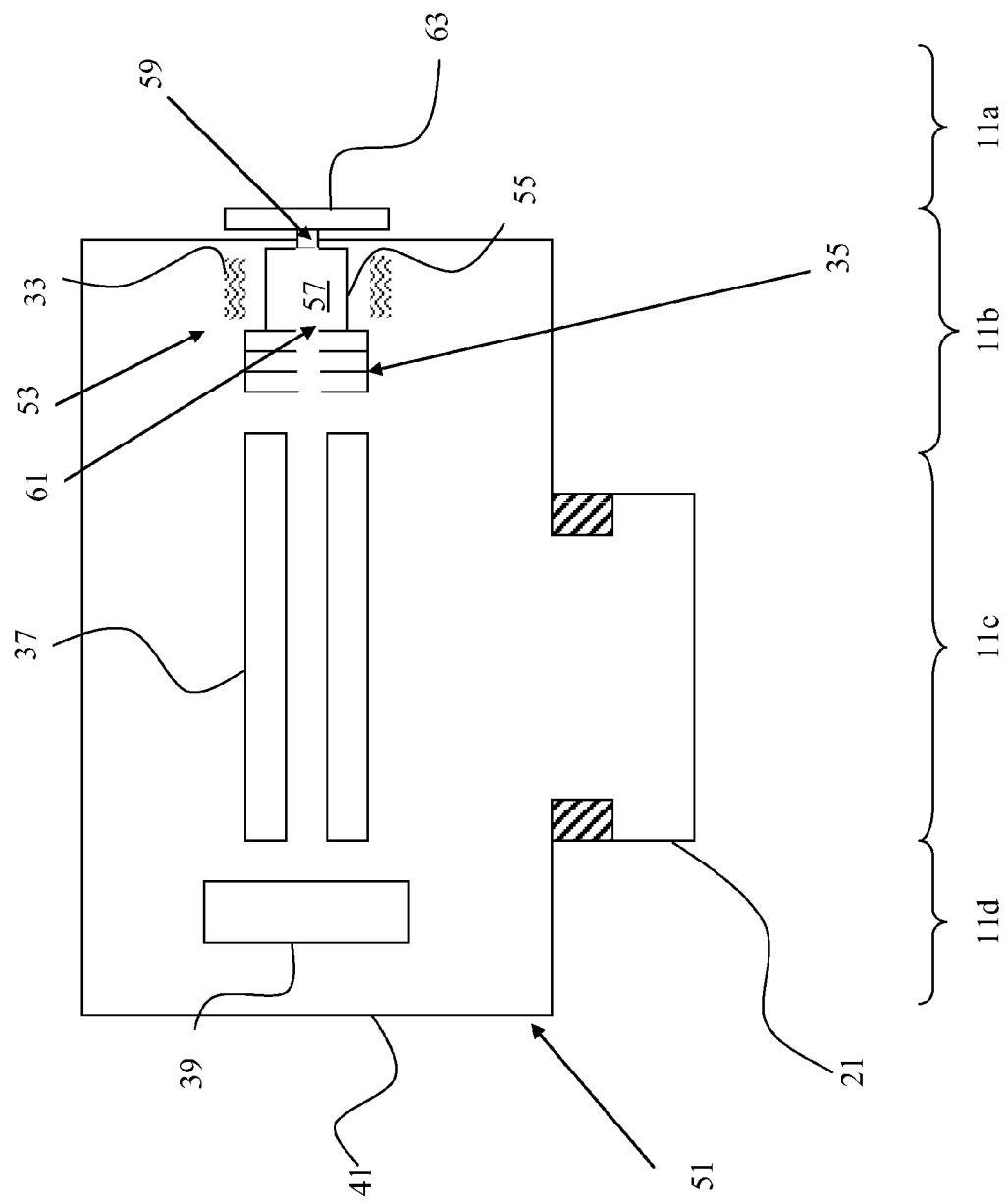
FIG. 2 is a block diagram of a gas analyser incorporating the ionisation device according to the present invention.

With reference to FIG. 2 a sampling device 53 according to the invention is schematically shown. The device, is being incorporated into a gas analyser denoted with the reference numeral 51. According to the present invention, the sampling device 53 comprises a high-vacuum tight casing 55 inside which a high-vacuum tight ionization chamber 57 is defined. Chamber 57 is provided with a first inlet hole 59 (for example, 2-3 mm long) for the entrance of the gas to be sampled and is connected to the ambient downstream through a second outlet hole 61 for the gas exit.

According to the present invention, the first hole 59 is separated from the outside ambient by a high-vacuum tight membrane 63 having at least a nanohole, i.e. a hole having a diameter in the order of nanometers i.e. with diameters in a range between 10 nm and 500 nm (for example, about 20 nm-30 nm). The membrane is substantially impermeable to the gas flow but that through the nanohole or nanoholes and preferably comprises only one nanohole or a limited number of nanoholes, (from ten to hundred nanoholes). The membrane 63, for instance with a square surface whose side is of about 100 μm and whose thickness is for instance of about 100 nm, is furthermore associated either with the walls of the ionization chamber 57 or with a duct associated therewith, through a high-vacuum tight coupling, for instance a suitable adhesive or a ring or a metal or VITON® gasket.

According to the invention the high-vacuum tight membrane 63 is provided with at least one nanohole having a diameter in the order of nanometers, which develops through the membrane 63 along a substantially rectilinear axis. Still according to the invention, the nanohole has a substantially uniform transverse cross-section.

According to a preferred embodiment of the invention, the membrane is substantially planar and the hole develops through the membrane along an axis, which is substantially perpendicular with respect to the surface of the membrane and has a substantially uniform transverse cross-section. Moreover the nanohole has a diameter D comprised between 10 nm and 500 nm.

The conductance C for a hole having a diameter in the order of nanometers (~100 nm), dividing two neighbouring spaces kept under differential vacuum conditions (of which one at atmospheric pressure (1,013 mbar) and the other one under high-vacuum conditions (typically below $10^{-2}$ Pa, in the shown example), is measurable as:

$$C = \left( \frac{1/4 \cdot (8 \cdot R \cdot T)}{\pi \cdot M} \right)^{1/2} \cdot A$$

where A is the hole surface, T is the gas temperature, R is the gas constant and M is the gas mass.

The concentration of the gas mixture when passing from the outside ambient to the ionization chamber 57 is therefore modified according to the above formula (gradually lighter gases will be present in higher concentrations inside the ionization chamber 57).

Inside the ionization chamber 57 the regime is however molecular and at the calibrated hole 61 for the exit of the ions towards the analyser again a molecular flow regime will occur, which will be still adjusted by the same formula (gradually lighter gases exit in higher amounts). In all, by suitably defining the hole 61 size, it will be therefore possible restoring inside the ionization chamber 57 the same concentration distribution of the different gases forming the gas mixture in the ambient in which the sampling takes place (outside ambient at atmospheric pressure in the shown example).

Hole 61 will therefore have a diameter in the order of mm, preferably in the range between 1 and 10 mm, for instance 2.5 mm and a length in the order of mm, for instance 1 mm.

It is known that in an electronic impact (EI) ion source, the bottom gas is ionised according to the equation:

$$I^+ = k_f \cdot I_e \cdot \sigma \cdot n \cdot l$$

where
$I_e$ is the emission current of the filament;
$\sigma$ is the ionisation impact section;
n is the gas density;
l is the electrons path inside the source;
$k_f$ is the collection efficiency of the produced ions,
which can be also written as:

$$I^+ = I_e \cdot K(k_f, \sigma, l) \cdot P(\beta, n)$$

where K is the sensibility of the ion source that for a hydrogen Bayart-Alpert gauge is $K=25$ torr$^{-1}$ ($19 \cdot 10^{-2}$ Pa$^{-1}$) and $\beta$ is a constant depending on the kind of the gas. Therefore, for a current $I_e = 4 \cdot 10^{-3}$ A at a pressure $P = 10^{-7}$ mbar ($10^{-5}$ Pa) the corresponding ion current will be:

$$I^+ \approx 10^{-9} A$$

If one would reach a sensibility in the order of 1 p.p.m. we will have:

$$I^+ \approx 10^{-15} A$$

that corresponds to an order of magnitude for instance measurable by means of a Channeltron detector. Moreover, being the minimum current measurable by this kind of detectors in the order of $10^{-19}$ A, it will be theoretically possible to reach sensibilities in the order of p.p.b. fractions.

With a nanohole diameter in the membrane 63 of about 30 nm, at 1 bar ($10^5$ Pa) a flow equal to:

$$\Phi = 2.3 \cdot 10^{-8} \text{ mbar} (2.3 \cdot 10^{-6} \text{ Pa})$$

will be obtained.

Assuming conductance of about 0.1 L/s through a hole 61 of about 2.0 mm diameter towards the quadrupole, inside the source a total pressure of about $10^{-7}$ mbar ($10^{-5}$ Pa) will occur, representing a value reachable for instance with a conventional ion pump.

Always according to the invention, the membrane 63 is of the kind able to be interposed in order to separate two spaces kept under differential vacuum conditions and having pressures $p_u$ and $p_d$ respectively, where $p_u > p_d$, and wherein the membrane 63 has at least an orifice or nanohole able to determine a controlled gas flow depending on pressure $p_u$, the orifice preferably having a diameter D and a length L predetermined such as $L < 20 \cdot D$.

Even more preferably, the membrane 63 is of the kind wherein the diameter D and the length L have sizes such as the equivalent diameter $D_e$ of the orifice is $D_e \leq 100$ nm, where $D_e$ is defined by the relationship $D_e = D \cdot a^{1/2}$, wherein a is the transmission probability of the orifice, depending on the L/D ratio, the orifice being able to operate under a molecular flow regime in a whole range of $P_u$ values comprising the atmospheric pressure value. The aforementioned condition has in fact resulted to be particularly effective to avoid "clogging" phenomena due to contaminants introduced in the device because of its exposure in air, or originated by oils backscattering of mechanical pumps used for vacuum generation or of other devices.

Preferably, the membrane 63 is made of ceramic, metallic, semiconductor material, or of a combination thereof, and the orifice is obtained by erosion with a highly focalised ion beam, commonly denoted with the acronym F.I.B.

Referring to FIG. 2, the sampling device 53 is incorporated into a gas analyser 51 comprising an entrance section 11a, an ionisation section 11b, an analysis section 11c and a detection section 11d. The entrance section 11a is intended for being immersed also in the atmosphere, i.e. for sampling gases at the atmospheric pressure, for the entrance of the gas to be sampled, or analyte, in the device and, according to the present invention, it incorporates the membrane 63. The ionisation section 11b comprises an ionisation chamber 57 for instance of the EI electronic impact kind and it is equipped with ionisation means 33, for instance ionisation filaments, or laser sources or radioactive sources or static plasma ionisation ones or radio-frequency ones. Electrostatic lenses 35 are provided downstream the ionisation chamber 57 in the transition area between the ion source and the following analysis section 11c. The analysis section 11c comprises a quadrupole device 37 and the detection section 11d comprises a detector 39, for instance a faraday cup detector and/or a SEM (or a Channeltron) detector. At least a high-vacuum pump 21, for instance an ion pump, is provided in association with the casing 41 of the device 51 to discharge the internal ambient inside which the analysis section 11c and the detection section 11d are housed.

Figure 1:
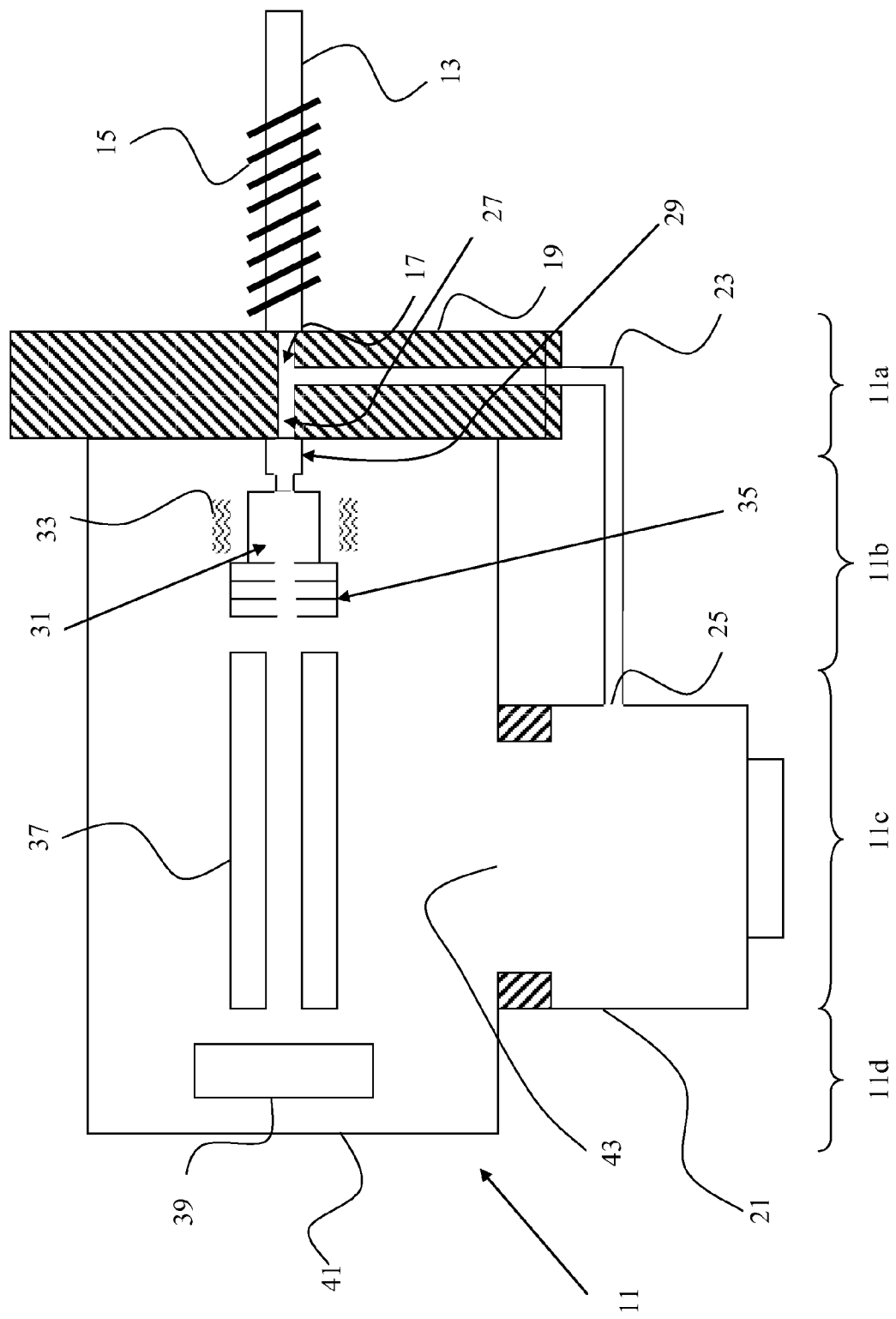
FIG. 1 is a block diagram of a gas analyser according to the prior art.

Advantageously, as it becomes evident from the comparison with the prior art configuration shown in FIG. 1, according to the invention the entrance section 11a is substantially reduced to only the membrane 63 with a resulting considerable simplification of the device and saving in the implementation cost. Such advantage becomes further evident for the fact that, according to the present invention, the high-vacuum pump can be submitted with a simple ion pump, due to the limited molecules flow passing through the membrane 63.

The molecular flow $\Phi$, which passes through the membrane 63 and, consequently, reaches the gas analyser 51 is linked to the conductance C through the relationship:

$$\Phi = C \cdot (p_u - p_d)$$

where $p_u$ and $p_d$ are the pressures outside and inside the chamber 57 respectively.

The contained sizes of the nanohole (for instance in the order of 20-30 nm) and of the volume of the sampling chamber 57 (for instance in the order of cm$^3$ or of cm$^3$ fractions) are a considerable advantage of the invention since they involve substantially reduced response times of the associated with the sampling device and they considerably reduce the deterioration problems of the device in case of use in presence of corrosive gases. Moreover, always due to the provision of the nanoholes membrane, it is possible to implement sampling devices considerably simplified and consequently capable of being implemented as portable configurations.

Figure 3:
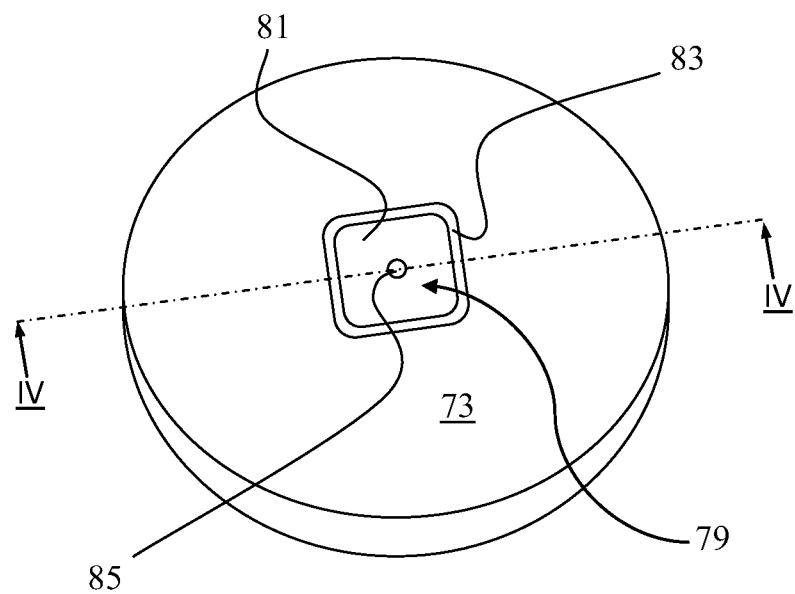
FIG. 3 is a perspective view of a support for an interface membrane.
Figure 4:
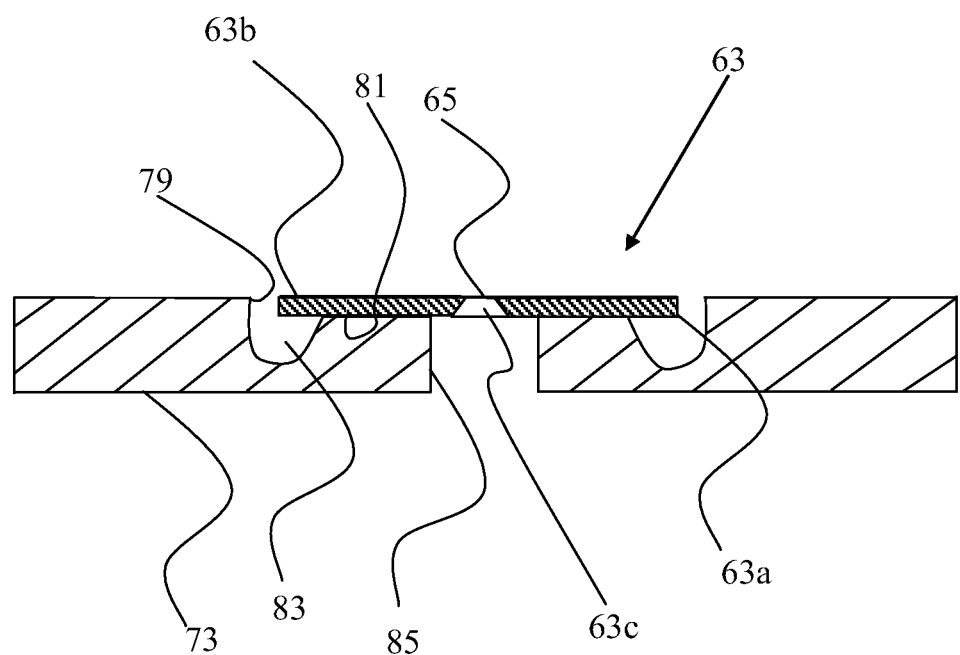
FIG. 4 is a section view taken along the line Iv-Iv of the support indicated in FIG. 3 when incorporating the membrane.

With reference to FIGS. 3 and 4, in a preferred embodiment of the present invention, the membrane 63 comprises a substrate 63a made of silicon (Si) and a surface cover layer 63b in silicon nitride (SiN). According to the invention, the layer 63b made of silicon nitride is preferably intended to face the space having higher pressure $p_u$, while the substrate 63a will face the space having lower pressure $p_d$. In an exemplary embodiment of the membrane 63, the substrate 63a and the layer 63b had a thickness of about 0.1-0.3 mm and respectively 200 nm.

According to the present invention, the membrane 63, in particular the face of the layer 63b, which is turned towards the space having higher pressure, can further be subjected, depending on the requests, to surface coating such as applying a waterproof coating, in order to avoid the water vapour generation, which could contribute to cause the event known as "clogging", the obstruction of the nanohole or nanoholes and consequently the interruption or reduction of the molecular flow of analyte from the section having higher pressure to the section at lower pressure.

In other embodiments, the membrane 63 can advantageously be associated to heating means which are still provided in order to avoid clogging risks. The membrane 63 is preferably accommodated in a support 73 advantageously provided with an appropriate well 79, wherein the membrane can be housed. Furthermore the support 73 is preferably made of metal, e.g. copper. The support 73 can have, for example, a disc-like shape having a diameter comprised between about 20 mm and 25 mm and a thickness comprised between about 1.5 mm ad 2.5 mm.

In the illustrated example, the well 79 is substantially defined at the centre of the support 73 and is a square, seen according to a plan view, into which a membrane 63 having preferably a complementary shape can be accommodated. In this exemplary embodiment, the membrane 63 can be for example a square, seen according to a plan view, having a side comprised between about 3.0 mm e 8.0 mm and a thickness of about 0.20 mm, and the well 79 can have a side length comprised between 5.0 mm and 10.0 mm.

Moreover the well 79 further comprises a resting zone 81 for the membrane 63, preferably located in the centre and positioned at a slightly lowered height with respect to the surface of the support 73, so that when the membrane 63 rests on the zone 81, the perimeter edges of the well 79 prevent the lateral escape of the membrane, thereby facilitating the mounting. In other words, it is sufficient that the perimeter sides of the well 79 determine a resting perimeter for the membrane 63 when this rests on the central zone 81.

The central zone 81 of the support 73 is further surrounded by a channel 83, in which an adhesive substance, e.g. a sealing resin, can be distributed in order to hold the membrane 63 on the support 73. The resting perimeter defined by the perimeter edges of the well 79 is further preferably spaced from the sides of the membrane 63 in order to allow the adhesive to flow out from the channel 83 when the membrane 63 is located on the resting zone 81 and to consent in this manner a perfect adhesion of the membrane 63 to the support 73. Advantageously, the channel 83 can be obtained by means of mechanical machining or by means of electrical discharge machining or laser ablation, so as to make preferably the inner surface to be rough in such a manner to guarantee the optimal adhesion of the adhesive material distributed thereon. The resting zone 81 of the support 83 further comprises an aperture 85 located at the nanohole 65 provided in the membrane 63. Clearly, if the membrane 63 had more than one nanohole, the aperture would be provided with a size and/or a number of apertures will be provided, which is/are adequate in order not to obstruct the nanoholes.

In the exemplary embodiment shown, the nanohole 65 is advantageously made at a thinner central zone 63c of the membrane 63, wherein the substrate 63a has been removed and there is only the layer 63b. The thinner zone is, for example, substantially a square with a side comprised between 20 and 500 micron. Other embodiments are however possible wherein the nanohole or nanoholes 65 are made in the membrane, without removing the substrate 63a or by removing it only partially. Accordingly the nanohole or nanoholes in the membrane 63 are made only in the layer 63b or in both the layer 63b and the substrate 63a. Moreover, according to the invention, the support 73, the respective well 79 and the membrane 63 can assume substantially any shape, e.g. circular, square, rectangular, rhombus-like, irregular, etc., according to the needs.

Though the invention has been disclosed with particular reference to an ion source of the EI electronic impact kind, it is however possible to provide the employment of the sampling device in combination with other kinds of source.

Moreover, though the invention has been disclosed with reference to an analyser of the quadrupole kind, it will be however possible for the man skilled in the art to employ the sampling device in other kinds of analysers, such as for instance the magnetic analysers, Omegatron analysers, ion-trap analysers, FI-ICR (Fourier Transform Ion Cyclotron Resonance) analysers, TOF (Time of Flight) analysers, cycloidal mass analysers, magnetic-sector and ion-trap analysers, optic spectroscopy cross-wire analysers.

According to a further aspect of the invention, the sampling device can be furthermore advantageously used in a predetermined gas leaks detector and it will therefore equipped with a specific mass spectrometer, considerably simplified with respect to the quadrupole, suitably tuned to detect the wanted gas. For instance, the sampling device according to the invention can be used in a helium leaks device wherein, as known, a current signal proportional to the concentration of helium ions in the ambient to be sampled is generated. Similarly, it will also be possible to take advantage of the device according to the invention in the field of leaks detection in devices using smelling probes.

The gas sampling device as described and shown is capable of many variants and modifications, all being parts of the same inventive principle.

What is claimed is:

1. A gas sampling device comprising:
    a high-vacuum tight ionization chamber defined within a high-vacuum tight casing, said ionization chamber defining a first inlet hole for receiving the gas to be ionised from an ambient outside the ionization chamber and a second outlet hole for outputting an ionised gas downstream from the ionization chamber; and
    a high-vacuum tight membrane separating the first hole from the ambient outside the ionization chamber and having at least one nanohole with a diameter in the order of nanometers, wherein said at least one nanohole is formed through the membrane along a substantially rectilinear axis.

2. The gas sampling device according to claim 1, wherein said nanohole has a substantially uniform transverse cross-section.

3. The gas sampling device according to claim 1, wherein the membrane is substantially planar and wherein said nanohole are formed through the membrane along an axis, which is substantially perpendicular with respect to a surface of the membrane and has a substantially uniform transverse cross-section.

4. The gas sampling device according to claim 1, wherein said nanohole has a diameter D being in a range between 10 nm and 500 nm.

5. The gas sampling device according to claim 1, wherein said membrane comprises a number of nanoholes ranging from one to hundred and wherein said membrane is substantially impermeable to the gas flow except through said nanohole or nanoholes.

6. The gas sampling device according to claim 1, wherein said membrane is of the type able to be interposed between two spaces having respective pressures $p_u$ and $p_d$, where $p_u > p_d$, and wherein said nanohole is capable of causing a controlled gas flow dependent on the pressure $p_u$, said nanohole having a predetermined diameter D and length L such that $L < 20 \cdot D$.

7. The gas sampling device according to claim 6, wherein the diameter D and the length L have sizes such that a diameter $D_e$ of an orifice is $D_e \leq 100$ nm, where $D_e$ is defined by the relationship $De = D \cdot a^{1/2}$, where a is the transmission probability of the orifice, which is function of the L/D ratio, said orifice being able to operate under molecular flow regime in a whole range of $P_u$ values comprising the value of the atmospheric pressure.

8. The gas sampling device according to claim 7, wherein the membrane is made of a material selected from the group consisting of ceramic, metallic, semiconductor material, and any combination of ceramic, metallic and semiconductor material.

9. The gas sampling device according to claim 1, further comprising electrostatic lenses for ion extraction, wherein said electrostatic lenses are associated with said second outlet hole.

10. The gas sampling device according to claim 1, wherein said outlet hole has a diameter in the order of millimeters, and being in a range between 1 and 3 mm.

11. The gas sampling device according to claim 1, further comprising a well for support of the membrane therein, said well comprises an aperture located at the nanohole of the membrane.

12. The gas sampling device according to claim 11, wherein the well further comprises a bearing zone adapted for the membrane and located at one height, which is slightly lowered with respect to a support surface, so that the perimeter edges of the well securing the membrane mounting on the bearing zone.

13. The gas sampling device according to claim 12, wherein a resting zone of the support for the membrane is surrounded by a channel, which accommodates an adhesive substance in for holding the membrane on the support surface.

14. A gas analyzer having an entrance section, an ionization section, an analysis section and a detection section, the gas analyzer comprising:
a high-vacuum tight casing;
a high-vacuum tight ionization chamber defined within said casing, said ionization chamber defining a first inlet hole for receiving the gas to be ionised from an ambient outside the ionization chamber and a second outlet hole for outputting an ionised gas downstream from the ionization chamber; and
a high-vacuum tight membrane separating the first inlet hole from the ambient outside the ionization chamber and having at least one nanohole with a diameter in the order of nanometers,
wherein said at least one nanohole is formed through the membrane along a substantially rectilinear axis.

15. The gas analyzer according to claim 14, wherein said analysis section comprises a quadrupole mass spectrometer.

16. The gas analyzer according to claim 15, wherein said entry section comprises the high-vacuum tight membrane.

17. The gas analyzer according to claim 16, wherein said ionization section comprises the ionization chamber and electrostatic lenses.

18. A gas sampling device, comprising:
an ionization chamber maintained in a high-vacuum condition and configured to ionize gas, the ionization chamber having an inlet hole for receiving the gas to be ionized from an ambient outside the ionization chamber and an outlet hole for outputting ionized gas downstream from the ionization chamber, the outside ambient being at atmospheric pressure; and
a membrane configured over the inlet hole to separate the ionization chamber from the outside ambient, the membrane defining at least one nanohole, with a diameter in the order of nanometers, enabling flow of the gas to be ionized into the inlet hole under differential vacuum conditions.

19. The gas sampling device of claim 18, wherein the membrane comprises:
a substrate; and
a surface cover layer formed on the substrate, wherein the at least one nanohole is defined through a thin central zone of the membrane formed by the surface cover layer.

20. The gas sampling device of claim 19, wherein the substrate comprises silicon (Si) and the surface cover layer comprises silicon nitride (SiN).

* * * * *